(12) United States Patent
Olson et al.

(10) Patent No.: US 8,066,685 B2
(45) Date of Patent: Nov. 29, 2011

(54) STRETCHABLE ABSORBENT ARTICLE HAVING LATERAL AND LONGITUDINAL STRETCH PROPERTIES

(75) Inventors: Christopher Peter Olson, Neenah, WI (US); James Marcus Carr, Kaukauna, WI (US); Lawrence Howell Sawyer, Neenah, WI (US); Michael John Faulks, Neenah, WI (US); Robert Lee Popp, Hortonville, WI (US); Mark Michael Mleziva, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1283 days.

(21) Appl. No.: 10/880,995

(22) Filed: Jun. 30, 2004

(65) Prior Publication Data

US 2006/0004341 A1 Jan. 5, 2006

(51) Int. Cl.
*A61F 13/15* (2006.01)
*A61F 13/20* (2006.01)

(52) U.S. Cl. .......... 604/385.22; 604/385.25; 604/385.27

(58) Field of Classification Search ............. 604/385.22, 604/385.29
See application file for complete search history.

(56) References Cited

U.S. PATENT DOCUMENTS

| | | | |
|---|---|---|---|
| 2,931,361 A | 4/1960 | Sostrin | |
| 3,849,241 A | 11/1974 | Butin et al. | |
| 3,921,638 A | 11/1975 | Schaar | |
| 3,978,861 A | 9/1976 | Schaar | |
| 4,036,233 A | 7/1977 | Kozak | |
| 4,050,462 A | 9/1977 | Woon et al. | |
| 4,100,324 A | 7/1978 | Anderson et al. | |
| 4,205,679 A | 6/1980 | Repke et al. | |
| 4,522,874 A | 6/1985 | Pommez | |
| 4,560,372 A | 12/1985 | Pieniak | |
| 4,573,986 A | 3/1986 | Minetola et al. | |
| 4,657,802 A | 4/1987 | Morman | |
| 4,663,220 A | 5/1987 | Wisneski et al. | |
| 4,704,114 A | 11/1987 | Wilson et al. | |
| 4,704,116 A | 11/1987 | Enloe | |
| 4,710,187 A * | 12/1987 | Boland et al. ............ | 604/385.22 |
| 4,720,415 A | 1/1988 | Vander Wielen et al. | |

(Continued)

FOREIGN PATENT DOCUMENTS

EP 0556749 A1 8/1993

(Continued)

OTHER PUBLICATIONS

U.S. Appl. No. 10/624,333, filed Jul. 22, 2003, Van Gompel, et al., Disposable Undergarment Having A Slit And Method For The Manufacture Thereof.

(Continued)

*Primary Examiner* — Melanie Hand
(74) *Attorney, Agent, or Firm* — Dority & Manning, P.A.

(57) ABSTRACT

Absorbent articles with carefully controlled stretch properties are disclosed. In particular, the articles exhibit stretch not only in the lateral direction but also in the longitudinal direction. Specifically, the articles have a biaxial stretch ratio, which refers to a ratio of stretch along the hip circumference of the article to the amount of stretch in the longitudinal direction, that is from about 1.0 to about 2.5, and particularly from about 1.1 to about 1.5. Absorbent articles made in accordance with the present invention are capable of accommodating a relatively large size range of wearers. The articles also exhibit improved fit and prevent sagging or drooping of the crotch region, even after the crotch region has been wetted.

30 Claims, 4 Drawing Sheets

U.S. PATENT DOCUMENTS

| | | | |
|---|---|---|---|
| 4,731,066 A | 3/1988 | Korpman | |
| 4,747,846 A | 5/1988 | Boland et al. | |
| 4,752,349 A | 6/1988 | Gebel | |
| 4,753,646 A | 6/1988 | Enloe | |
| 4,756,709 A | 7/1988 | Stevens | |
| 4,808,176 A | 2/1989 | Kielpikowski | |
| 4,834,736 A | 5/1989 | Boland et al. | |
| 4,846,823 A | 7/1989 | Enloe | |
| 4,854,995 A | 8/1989 | Kasper et al. | |
| 4,865,597 A | 9/1989 | Mason, Jr. et al. | |
| 4,874,451 A | 10/1989 | Boger et al. | |
| 4,892,536 A | 1/1990 | DesMarais et al. | |
| 4,935,021 A | 6/1990 | Huffman et al. | |
| 4,938,755 A | 7/1990 | Foreman | |
| 4,940,464 A | 7/1990 | Van Gompel et al. | |
| 4,990,147 A | 2/1991 | Freeland | |
| 5,026,364 A | 6/1991 | Robertson | |
| 5,037,416 A | 8/1991 | Allen et al. | |
| 5,046,272 A | 9/1991 | Vogt et al. | |
| 5,104,116 A | 4/1992 | Pohjola | |
| 5,114,781 A | 5/1992 | Morman | |
| 5,116,662 A | 5/1992 | Morman | |
| 5,151,092 A | 9/1992 | Buell et al. | |
| 5,224,405 A | 7/1993 | Pohjola | |
| 5,226,992 A | 7/1993 | Morman | |
| 5,256,405 A | 10/1993 | Chappell et al. | |
| 5,269,775 A | 12/1993 | Freeland et al. | |
| 5,284,703 A | 2/1994 | Everhart et al. | |
| 5,340,424 A | 8/1994 | Matsushita | |
| 5,350,624 A | 9/1994 | Georger et al. | |
| 5,368,584 A | 11/1994 | Clear et al. | |
| 5,397,316 A | 3/1995 | LaVon et al. | |
| 5,397,317 A | 3/1995 | Thomas | |
| 5,455,992 A | 10/1995 | Kurschatke et al. | |
| 5,486,166 A | 1/1996 | Bishop et al. | |
| 5,490,846 A | 2/1996 | Ellis et al. | |
| 5,503,076 A | 4/1996 | Yeo | |
| 5,554,143 A | 9/1996 | Roe et al. | |
| 5,593,401 A | 1/1997 | Sosalla et al. | |
| 5,611,790 A | 3/1997 | Osborn, III et al. | |
| 5,624,422 A | 4/1997 | Allen | |
| 5,634,916 A | 6/1997 | Lavon et al. | |
| 5,643,242 A | 7/1997 | Lavon et al. | |
| 5,645,542 A | 7/1997 | Anjur et al. | |
| 5,658,269 A | 8/1997 | Osborn, III et al. | |
| 5,690,627 A | 11/1997 | Clear et al. | |
| 5,695,868 A | 12/1997 | McCormack | |
| 5,766,389 A | 6/1998 | Brandon et al. | |
| 5,804,021 A | 9/1998 | Abuto et al. | |
| 5,817,086 A | 10/1998 | Kling | |
| 5,820,973 A | 10/1998 | Dodge, II et al. | |
| 5,843,056 A | 12/1998 | Good et al. | |
| 5,846,232 A | 12/1998 | Serbiak et al. | |
| 5,873,868 A | 2/1999 | Nakahata | |
| 5,883,028 A | 3/1999 | Morman et al. | |
| 5,914,184 A | 6/1999 | Morman | |
| 5,928,211 A | 7/1999 | Gustafsson et al. | |
| 5,947,947 A | 9/1999 | Tanzer et al. | |
| 5,957,907 A | 9/1999 | Sauer | |
| 5,964,743 A | 10/1999 | Abuto et al. | |
| 5,997,981 A | 12/1999 | McCormack et al. | |
| 6,049,915 A | 4/2000 | Malowaniec | |
| 6,093,870 A | 7/2000 | Carlsson | |
| 6,103,953 A | 8/2000 | Cree et al. | |
| 6,120,485 A | 9/2000 | Gustafsson et al. | |
| 6,129,720 A | 10/2000 | Blenke et al. | |
| 6,132,411 A | 10/2000 | Huber et al. | |
| 6,149,638 A | 11/2000 | Vogt et al. | |
| 6,149,934 A | 11/2000 | Krzysik et al. | |
| 6,160,197 A | 12/2000 | Lassen et al. | |
| 6,174,303 B1 | 1/2001 | Suprise et al. | |
| 6,193,701 B1 | 2/2001 | Van Gompel et al. | |
| 6,217,563 B1 | 4/2001 | Van Gompel et al. | |
| 6,231,557 B1 | 5/2001 | Krautkramer et al. | |
| 6,262,331 B1 | 7/2001 | Nakahata et al. | |
| 6,264,639 B1 | 7/2001 | Sauer | |
| 6,264,641 B1 | 7/2001 | Van Gompel et al. | |
| 6,312,786 B1 | 11/2001 | Schwinn | |
| 6,362,389 B1 | 3/2002 | McDowall et al. | |
| 6,383,431 B1 | 5/2002 | Dobrin et al. | |
| 6,409,711 B1 | 6/2002 | Jönbrink | |
| 6,413,247 B1 | 7/2002 | Carlucci et al. | |
| 6,461,338 B1 | 10/2002 | Shimoe et al. | |
| 6,482,191 B1 | 11/2002 | Roe et al. | |
| 6,521,811 B1 | 2/2003 | Lassen et al. | |
| 6,552,245 B1 | 4/2003 | Roessler et al. | |
| 6,570,056 B1 | 5/2003 | Tanzer et al. | |
| 6,572,598 B1 | 6/2003 | Ashton et al. | |
| 6,582,414 B1 | 6/2003 | Richardson | |
| 6,595,975 B2 | 7/2003 | Vogt et al. | |
| 6,610,383 B1 | 8/2003 | Morman et al. | |
| 6,623,465 B1 | 9/2003 | Roe et al. | |
| 6,632,212 B1 | 10/2003 | Morman et al. | |
| 6,641,568 B2 | 11/2003 | Ashton et al. | |
| 6,645,190 B1 | 11/2003 | Olson et al. | |
| 6,679,869 B1 | 1/2004 | Schlinz et al. | |
| 6,682,512 B2 | 1/2004 | Uitenbroek et al. | |
| 6,702,799 B2 | 3/2004 | Otsubo | |
| 6,702,800 B1 | 3/2004 | Vukos et al. | |
| 6,703,538 B2 | 3/2004 | Lassen et al. | |
| 6,706,028 B2 | 3/2004 | Roe et al. | |
| 6,746,976 B1 * | 6/2004 | Urankar et al. | 442/155 |
| 6,755,808 B2 | 6/2004 | Balogh et al. | |
| 6,840,928 B2 * | 1/2005 | Datta et al. | 604/385.22 |
| 6,969,378 B1 * | 11/2005 | Vukos et al. | 604/385.22 |
| 7,011,653 B2 | 3/2006 | Imsangjan et al. | |
| 2002/0058922 A1 | 5/2002 | Skog | |
| 2002/0099352 A1 | 7/2002 | Heden et al. | |
| 2002/0104608 A1 | 8/2002 | Welch et al. | |
| 2002/0165516 A1 | 11/2002 | Datta et al. | |
| 2003/0023213 A1 | 1/2003 | Fernfors et al. | |
| 2003/0120243 A1 * | 6/2003 | Uitenbroek et al. | 604/385.16 |
| 2003/0125696 A1 * | 7/2003 | Morman et al. | 604/385.22 |
| 2003/0208171 A1 | 11/2003 | Zehner et al. | |
| 2004/0013850 A1 | 1/2004 | Kling | |
| 2004/0044323 A1 | 3/2004 | Roessler et al. | |
| 2004/0102749 A1 | 5/2004 | Olson et al. | |
| 2004/0127878 A1 | 7/2004 | Olson et al. | |
| 2004/0127881 A1 | 7/2004 | Stevens et al. | |
| 2006/0035055 A1 | 2/2006 | Schneider et al. | |

FOREIGN PATENT DOCUMENTS

| | | |
|---|---|---|
| EP | 0957868 B1 | 11/1999 |
| GB | 2284538 A | 6/1995 |
| GB | 2305610 A | 4/1997 |
| GB | 2310606 A | 9/1997 |
| GB | 2325146 A | 11/1998 |
| WO | WO 9519753 A1 | 7/1995 |
| WO | WO 9852506 A1 | 11/1998 |
| WO | WO 9306805 A1 | 4/1999 |
| WO | WO 0037009 A2 | 6/2000 |
| WO | WO 0037009 A3 | 6/2000 |
| WO | WO 01/15645 | 3/2001 |
| WO | WO 0234184 A1 | 5/2002 |
| WO | WO 03057106 A1 | 7/2003 |
| WO | WO 2004020174 A1 | 3/2004 |
| WO | WO 2004108041 A1 | 12/2004 |

OTHER PUBLICATIONS

U.S. Appl. No. 10/646,978, filed Aug. 22, 2003, McCormack, et al., Microporous Breathable Eleastic Films, Methods Of Making Same, And Limited Use Or Disposable Product Applications.

U.S. Appl. No. 10/703,761, filed Nov. 7, 2003, Van Gompel, et al., Microporous Breathable Elastic Films, Methods Of Making Same, And Limited use Or Disposable Product Applications.

U.S. Appl. No. 10/743,245, filed Dec. 22, 2003, Maldonado, et al., Extensible And Stretch Laminates And Method Of Making Same.

U.S. Appl. No. 10/749,366, filed Dec. 31, 2003, Van Gompel, et al., Disposable Garment Having An Elastic Inner Layer With A Narrow Width In The Crotch Region.

U.S. Appl. No. 10/749,368, filed Dec. 31, 2003, Van Gompel, et al., Dual-Layered Disposable Garment Having An Optimized Fastening System.

U.S. Appl. No. 10/749,761, filed Dec. 31, 2003, Van Gompel, et al., Dual-Layered Disposable Garment Having Tailored Stretch Characteristics.

U.S. Appl. No. 10/750,253, filed Dec. 31, 2003, Van Gompel, et al., Disposable Garment Having A Light Framework And Flexible Waist Closure.

U.S. Appl. No. 10/750,402, filed Dec. 31, 2003, Van Gompel, et al., Dual-Layered Disposable Garment.

U.S. Appl. No. 10/835,528, filed Apr. 29, 2004, Sawyer, et al., Absorbent Garments With Form-Fitting Properties.

U.S. Appl. No. 10/881,718, filed Jul. 30, 2004, Sawyer, et al., Absorbent Garments With Tailored Stretch Properties In The Lateral Direction.

Translation of Japanese Patent No. JP60194947, 8 pages, Oct. 3, 1985.

PCT Search Report and Written Opinion for PCT/US2005/002438, Jun. 29, 2005.

"Polyethylene—Low Density (LDPE)—Material Information," Internet web page "http://www.goodfellow.com/csp/active/STATIC/E/Polyethylene_-_Low_Density.HTML", p. 3, line 1, Goodfellow Corporation, Devon, PA.

PCT Search Report and Written Opinion for PCT/US2005/014167, Aug. 1, 2005.

Search Report and Written Opinion for PCT/US2005/011052, Sep. 1, 2005.

\* cited by examiner

STRETCHABLE ABSORBENT ARTICLE HAVING LATERAL AND LONGITUDINAL STRETCH PROPERTIES

BACKGROUND OF THE INVENTION

Absorbent articles such as diapers, training pants, incontinence garments, swim pants, fitted briefs and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary and/or to provide a better fit on the wearer. For example, some absorbent articles have been made in the past that include leg elastics for providing a secure fit around the legs of a user. Absorbent articles have also been made containing waist elastic members that allow the waist of the article to expand and contract. Elastic members surrounding the waist of a wearer not only provide the article with some form-fitting properties but also allow the article to accommodate a range of sizes.

Producing an absorbent article that possesses a wide range of fit may provide various benefits not only to the manufacturer of the article but also to the consumer. For instance, consumers commonly buy disposable absorbent articles that are not technically the correct size for the wearer. For example, consumers may attempt to save money by buying a smaller sized product or, instead, may purchase a larger sized product in order to have extra absorbency. In other cases, a parent may not know the exact weight of their child and purchase the wrong size.

Although some products made in the past may accommodate some variety in sizes, a need remains for an absorbent product that can not only accommodate a range of sizes but also exhibits improved fit properties over the entire range. In particular, a need exists for an absorbent article that can not only accommodate a wide range of sizes but also does not droop or sag in the crotch area after being wetted.

SUMMARY OF THE INVENTION

In general, the present invention relates to disposable absorbent articles having carefully controlled biaxial stretch properties, i.e., controlled stretch properties in both the longitudinal and lateral directions. The absorbent articles may have form-fitting properties resulting in an improved fit and appearance. Of particular advantage, the stretch properties of the articles made according to the present invention have been designed to substantially match the growth rates of infants and small children in terms of increases in hip circumference and increases in the height of the wearer (which corresponds to increases in crotch length) based on anthropomorphic data.

Specifically, the Assignee of the present invention has conducted numerous internal studies that indicate that as the weight of an infant or child increases, the average hip circumference increases 1.3 times more than the average rise in the longitudinal direction. These studies have focused mainly on infants and children from 0-80 months old. By designing a garment in accordance with the findings of the above studies, the garment is capable of snuggly and comfortably fitting infants and children in a relatively wide age zone.

For instance, by controlling the stretch properties of the absorbent articles in the lateral direction and the longitudinal direction as described above, the articles may advantageously fit a substantially large size range. The articles, in fact, can accommodate a relatively large size range while still preventing against sagging or drooping in the crotch region, even after the article has been wetted. Specifically, the crotch region is maintained in close contact with the body during use over the entire range of sizes.

For example, in one embodiment, the present invention is directed to a biaxially stretchable absorbent article comprising an outer cover. The outer cover may be biaxially stretchable and, in some embodiments, biaxially elastic. The outer cover, for instance, may comprise a biaxially elastic film or a biaxially elastic laminate containing a nonwoven material. A biaxially stretchable bodyside liner is joined to the outer cover in a superimposed relation. The liner may be elastic in some applications.

An absorbent structure is positioned in between the outer cover and the liner. The outer cover, liner and absorbent structure form a chassis. The absorbent article includes a front region, a back region, and a crotch region. The front region and back region define a waist opening when worn about a wearer. The crotch region is positioned between two leg openings that are located opposite the waist opening.

The absorbent article further includes a longitudinal direction extending from the front region, through the crotch region and to the back region. In other words, the longitudinal direction extends from a front waist edge to a back waist edge. The absorbent article further includes a lateral direction generally parallel to the circumference of the waist opening and perpendicular to the longitudinal direction. The absorbent article includes a hip circumference in the lateral direction that is located so as to circumscribe the hips of a wearer. In accordance with the present invention, the absorbent article is stretchable so as to have a biaxial stretch ratio of from about 1.0 to about 2.5. The biaxial stretch ratio is defined by the following formula:

$$\text{Biaxial Stretch Ratio} = \frac{\%\ \text{Stretch Along the Hip Circumference}}{\%\ \text{Stretch in the Longitudinal Direction}}$$

wherein:

$$\%\ \text{Stretch Along the Hip Circumference} = \frac{\left(\text{Hip Circumference at 2000 g} - \text{Hip Circumference at 70 g}\right)}{\text{Hip Circumference at 70 g}} \times 100$$

$$\%\ \text{Stretch in the Longitudinal Direction} = \frac{\left(\text{Length of Article at 500 g} - \text{Length of Article at 70 g}\right)}{\text{Length of Article at 70 g}} \times 100$$

In accordance with the present invention, the biaxial stretch ratio within the above range may vary depending upon the particular circumstances. For instance, in one embodiment, the biaxial stretch ratio may be from about 1.3 to about 2.0, such as from about 1.1 to about 1.5. In other embodiments, the biaxial stretch ratio may be less than about 1.3 in order to minimize sagging or drooping of the product when the product has been insulted with body fluids. Conversely, in a product designed to hold relatively small amounts of liquids, the biaxial ratio may be larger than about 1.3 in order to provide greater amounts of longitudinal stretch.

In constructing absorbent articles with the above stretch properties, various elastic components may be incorporated into the articles that contribute to the stretch characteristics. For instance, the absorbent article may include opposing pairs of front and back side panels that extend laterally from the chassis. The front and back side panels may be elastic in at least the lateral direction and may be in operative association with an attachment device for attaching the article around the waist of a wearer. The attachment device may be, for instance, hook and loop fasteners or an adhesive fastener in conjunction with a corresponding adhesive-receptive landing zone.

In addition to front and back side panels, the absorbent article may further include a pair of elastic containment flaps that extend generally in the longitudinal direction along at least the crotch region of the article. The elastic containment flaps are contained inside the article and may be attached, for instance, to the liner for preventing liquids from escaping the article. Similarly, the absorbent article may further include a pair of leg elastic members that at least partially surround the leg openings for maintaining the leg openings against the legs of a wearer.

Within the above described biaxially stretch ratio ranges, the percent stretch of the article in the longitudinal direction may be from about 5% to about 30%, such as from about 10% to about 25%. For instance, in one embodiment, the percent stretch in the longitudinal direction may be from about 15% to about 20%.

In some embodiments, the stretch in the longitudinal direction may desirably be concentrated in the waist area of the article. For instance, the absorbent article may include a front waist zone and a back waist zone that each comprise from about 15% to about 20% of the total length of the article. At least about 80% of the stretch in the longitudinal direction may reside in the waist zones, such as at least about 90% of the stretch in the longitudinal direction. Maintaining greater amounts of longitudinal stretch in the waist zones may further prevent sagging or drooping of the article over a wide range of sizes.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
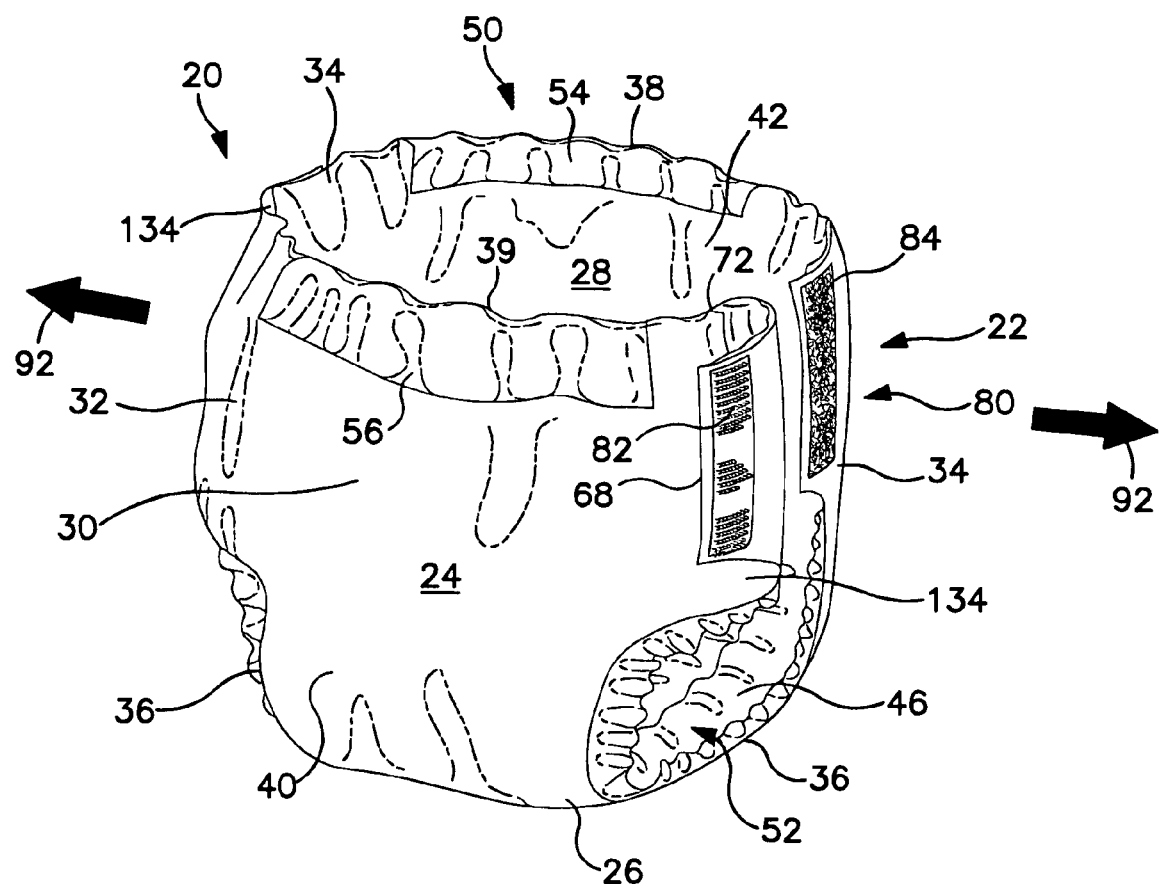
FIG. 1 is a perspective view of one embodiment of an absorbent article that may be made in accordance with the present invention.

Repeated use of reference characters in the present specification and drawings is intended to represent the same or analogous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention.

In general, the present invention is directed to absorbent articles designed to provide improved dry and wet fit for a relatively large range of sizes. The absorbent article may be, for instance, a diaper, a toilet training pant, an adult incontinence garment, a swim pant, a fitted brief, or the like. Absorbent garments made according to the present invention have stretch in at least two dimensions. In particular, the absorbent articles have stretch properties in the longitudinal direction of the product and in the lateral or transverse direction of the product. The longitudinal stretch extends from a front waist edge of the product to a back waist edge. The lateral stretch, on the other hand, exists at least within the hip circumference of the product, which is located where the product encircles the hips of a user.

More particularly, absorbent articles made in accordance with the present invention have carefully controlled stretch properties in both the longitudinal and lateral directions. Specifically, the stretch properties in one direction are controlled relative to the percentage of stretch in a perpendicular direction. For instance, absorbent articles made in accordance with the present invention are biaxially stretchable so as to have a biaxial stretch ratio of from about 1.0 to about 2.5. The biaxial stretch ratio is defined by the following formula:

$$\text{Biaxial Stretch Ratio} = \frac{\text{\% Stretch Along the Hip Circumference}}{\text{\% Stretch in the Longitudinal Direction}}$$

wherein:

$$\frac{\text{\% Stretch Along}}{\text{the Hip Circumference}} = \frac{\left(\begin{array}{c}\text{Hip Circumference at 2000 g} - \\ \text{Hip Circumference at 70 g}\end{array}\right)}{\text{Hip Circumference at 70 g}} \times 100$$

$$\frac{\text{\% Stretch in the}}{\text{Longitudinal Direction}} = \frac{\left(\begin{array}{c}\text{Length of Article at 500 g} - \\ \text{Length of Article at 70 g}\end{array}\right)}{\text{Length of Article at 70 g}} \times 100$$

and wherein the hip circumference of the product is defined as the circumferential area that is generally parallel to the waist opening and comprises the lower two-thirds of the side panels. In other words, the hip circumference is a circumferential band that extends 66% of the distance from the top of the leg openings on the chassis towards the waist opening.

Absorbent articles having the above described biaxial stretch properties provide various benefits and advantages. For instance, articles made according to the present invention can accommodate a broad range of sizes, reducing the number of size ranges that the manufacturer needs to produce. As stated in the background section above, consumers are known, for many reasons, to purchase disposable absorbent garments that are not correctly sized to the user. Thus, producing absorbent garments capable of accommodating a greater size range also provides benefits to the consumer by reducing the likelihood of purchasing the wrong size. Further, products made according to the present invention may provide at least some amount of adequate fit even outside of an advertised fit range.

In addition to accommodating a broad range of sizes, absorbent articles made according to the present invention provide a snug and comfortable fit about the wearer. The articles are capable of containing bodily fluids even within a relatively broad range of sizes.

In the past, some absorbent garments have been made with transverse stretch, such as around the waist of the garment.

Transverse or lateral stretch may be used to provide automatically adjustable fit and comfort over a limited range of body geometries. As hip circumference increases, however, the rise dimension of a user also increases albeit at a lower rate of change. In this regard, articles that only provide transverse stretch properties become limited in the range of sizes that the article can accommodate and reach a point of diminishing return and consumer acceptable fit for each unit increase in elongation. Specifically, articles that only provide for transverse stretch become too short when undersized and tend to sag and droop when oversized.

Absorbent articles made according to the present invention, however, have biaxial stretch properties not only in the lateral direction but also in the longitudinal direction. More particularly, absorbent articles made according to the present invention are designed based upon anthropometric data which indicates that as the weight of an individual, such as an infant or child, increases, the average hip circumference increases 1.3 times more than the average rise in the longitudinal direction. Thus, products made according to the present invention are designed to have a stretch ratio of percent stretch along the hip circumference to the percent stretch in the longitudinal direction of from about 1.0 to about 2.3. By matching stretch properties in the lateral and longitudinal direction with the expected growth rate of a user significantly and synergistically extends the range of fit in that the product is capable of automatically being adjusted for increases and decreases in the rise in comparison to increases and decreases in the hip circumference. Thus, products made according to the present invention that are undersized for a user or oversized for a user still provide the necessary fit, comfort and performance required by consumers. Further, the stretch properties of the present invention also prevent against drooping or sagging of the absorbent article in the crotch region when the product is undersized or should the product be insulted with body fluids.

In general, the absorbent articles are made with stretchable and/or elastic materials. As used herein, the term "stretchable" refers to a material that may be extensible and/or elastic (or elastomeric). That is, the material may be extended, deformed or the like, without breaking, and may or may not significantly retract after removal of an extending force. The terms "elastic" or "elastomeric" are used interchangeably herein and refer to a property of a material where upon removal of an elongating force, the material was capable of recovering to substantially its unstretched size and shape or the material exhibits a significant retractive force. The term "extensible" refers to a property of a material where upon removal of an elongating force, the material experiences a substantially permanent deformation or the material does not exhibit a significant retractive force. In particular, elastic materials utilized in connection with the present invention may be elongated/extended or stretched in at least one direction and desirably in at least two directions without breaking by at least 15%, such as by at least 25% (to at least 125% of its initial unstretched length) in at least one direction, suitably by at least 50% (to at least 150% of its initial unstretched length) and which will recover, upon release of the applied stretching or biasing force, at least 10% of their elongation. It is generally advantageous that the elastomeric material or composite be capable of being elongated by at least 100%, more desirably at least 200%, of its relaxed length and recover at least 30% and more desirably 50% of its elongation upon release of a stretching, biasing force, within about one minute.

Absorbent articles having a biaxial stretch ratio as described above can be designed in various ways as would be apparent to one skilled in the art. For example, in one embodiment, the absorbent article can include a chassis that is stretchable in the longitudinal and the lateral directions. The chassis can include at least one layer of material that is elastic. For example, in one embodiment, the elastic material may comprise a laminate, such as a stretch bonded laminate or a neck bonded laminate, that includes an elastic layer laminated to a nonelastic layer. The elastic layer may be biaxially stretchable. In accordance with the present invention, the nonelastic layer may be connected or attached to the elastic layer in a manner that controls the stretch properties of the elastic layer so that the elastic layer has a biaxial stretch ratio as desired. For instance, the nonelastic layer may be a gathered layer that permits the elastic layer to stretch more in the transverse direction than in the longitudinal direction.

Referring to FIG. 1, for exemplary purposes, an absorbent article 20 that may be made in accordance with the present invention is shown. The absorbent article 20 may or may not be disposable, which refers to articles that are intended to be discarded after a limited period of use instead of being laundered or otherwise conditioned for reuse. It is understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention may be disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 2:
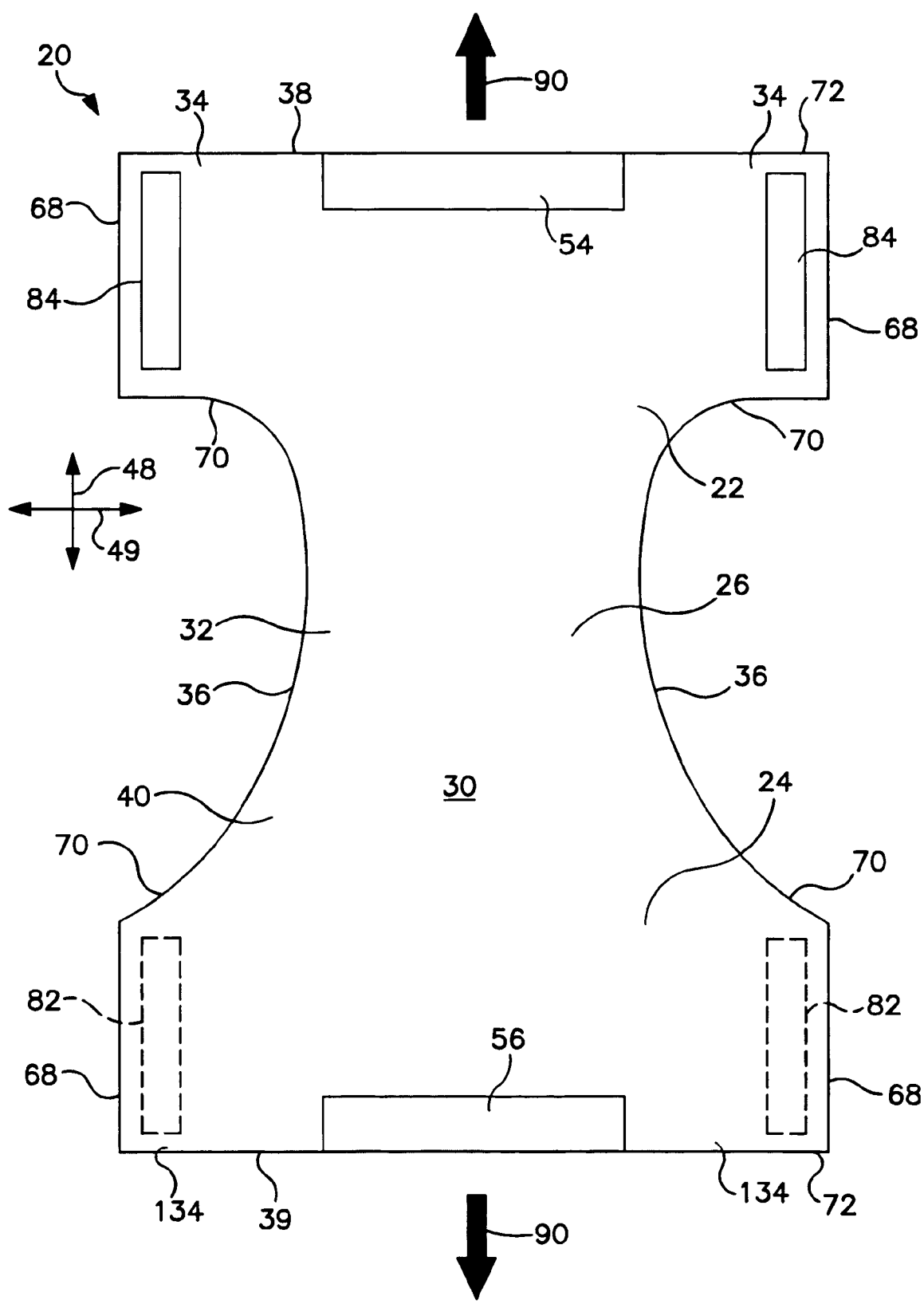
FIG. 2 is a plan view of the absorbent article shown in FIG. 1 with the article in an unfastened, unfolded and laid flat condition showing the surface of the article that faces away from the wearer.
Figure 3:
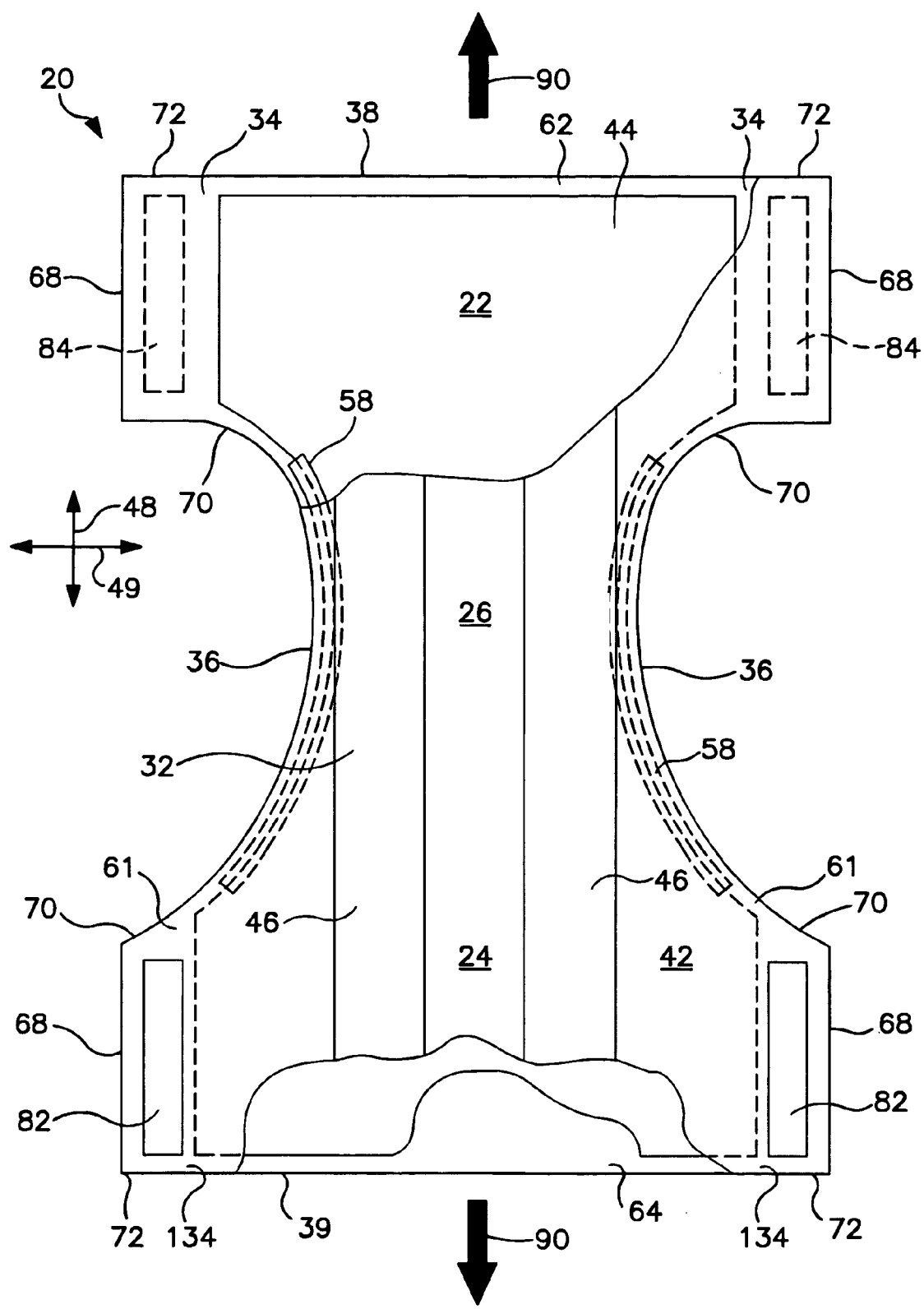
FIG. 3 is a plan view similar to FIG. 2 showing the surface of the absorbent article that faces the wearer when worn and with portions cut away to show underlying features.

A pair of training pants 20 is representatively illustrated in FIG. 1 in a partially fastened condition. The training pants 20 shown in FIG. 1 is also represented in FIGS. 2 and 3 in an opened and unfolded state. Specifically, FIG. 2 is a plan view illustrating the exterior side of the pants 20, while FIG. 3 illustrates the interior side of the pants 20. As shown in FIGS. 2 and 3, the pants 20 defines a longitudinal direction 48 that extends from the front of the training pants when worn to the back of the training pants. Opposite to the longitudinal direction 48 is a lateral direction 49.

The pants 20 define a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The training pants 20 have a pair of laterally opposite side edges 36 and a pair of longitudinally opposite waist edges, respectively designated front waist edge 38 and back waist edge 39.

The illustrated pants 20 may include a chassis 32, a pair of laterally opposite front side panels 34 extending laterally outward at the front region 22 and a pair of laterally opposite back side panels 134 extending laterally outward at the back region 24.

Referring to FIGS. 1-3, the chassis 32 includes an outer cover 40 and a bodyside liner 42 (FIGS. 1 and 3) that may be joined to the outer cover 40 in a superimposed relation therewith by adhesives, ultrasonic bonds, thermal bonds or other conventional techniques. Referring to FIG. 3, the liner 42 may suitably be joined to the outer cover 40 along the perimeter of the chassis 32 to form a front waist seam 62 and a back waist seam 64. As shown in FIG. 3, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants. The chassis 32 may further include an absorbent structure 44 particularly shown in FIG. 3 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

With the training pants 20 in the fastened position as partially illustrated in FIG. 1, the front and back side panels 34, 134 can be connected together by a fastening system 80 to define a three-dimensional pants configuration having a waist opening 50 and a pair of leg openings 52. The front and back side panels 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The elasticized containment flaps 46 as shown in FIG. 3 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may also suitably include a front waist elastic member 54 (FIG. 1), a rear waist elastic member 56, and leg elastic members 58 (FIG. 3), as are known to those skilled in the art. The waist elastic members 54 and 56 can be operatively joined to the outer cover 40 and/or the bodyside liner 42 and can extend over part or all of the waist edges 38, 39. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

As shown in FIGS. 1 through 3, the side panels 34 and 134 can be formed as an integral portion of the chassis 32. For example, the side panels 34, 134 can include a generally wider portion of the outer cover 40, the bodyside liner 42, and/or other components of the chassis 32. As described above, the side panels 34 and 134 may be attached together using any suitable fastening system 80.

In the embodiments shown in the figures, the side panels 34 and 134 are releaseably attachable. It should be understood, however, that in other embodiments the side panels 34 and 134 may be permanently joined together. For instance, the side panels may be made from a unitary piece of material. Alternatively, the side panels may be bonded together using ultrasonic bonding, thermal bonding or an adhesive. In this embodiment, the absorbent article is pulled over the legs when being worn.

Figure 4:
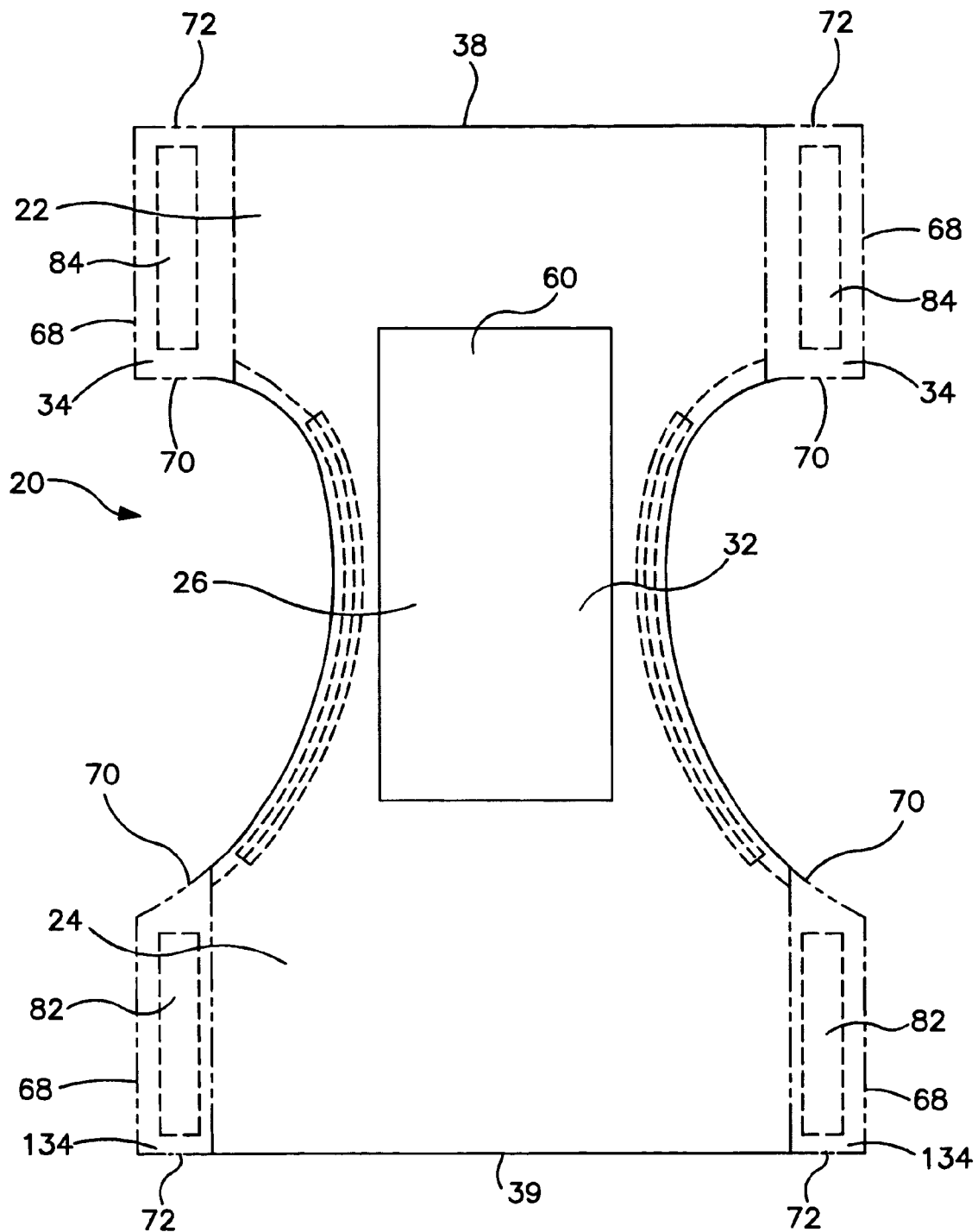
FIG. 4 is another embodiment of a plan view of an absorbent article made in accordance with the present invention showing the surface of the article that faces the wearer. In this embodiment, the article includes laterally extending front and back side panels that are separate from and attached to the chassis of the absorbent article.

Referring to FIG. 4, in an alternative embodiment of the present invention, the side panels 34 and 134 may be separately attached to the chassis 32. For instance, the front side panels 34 can be permanently bonded to and extend transversely outward beyond the side margins of the chassis 32. Similarly, the back side panels 134 can be permanently bonded to and extend transversely outward beyond the side margins of the chassis 32 and the back region 24. The side panels 34 and 134 may be bonded to the chassis 32 using attachment means known to those skilled in the art such as adhesive, thermal or ultrasonic bonding.

The front and back side panels 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side panels 34 and 134 form part of the pant side edges 36 of the training pants 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants. In the figures, the waist end edges 72 and the outer edges 68 are generally horizontal and vertical respectively. It should be understood, however, that in other embodiments, the waist end edges 72 and/or the outer edges 68 may have a curved, slanted or complex arrangement depending upon the particular application.

In configurations where the side panels 34, 134 are separately attached, such as shown in FIG. 4, the side panels may be provided by an elastic material capable of stretching at least in a direction generally parallel to the lateral direction 49 of the training pants 20. Suitable elastic materials, as well as one process of incorporating elastic side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith. Alternatively, the side panel material may include other woven or non-woven materials, such as those described later herein as being suitable for construction of the outer cover 40 and/or the bodyside liner 42; mechanically pre-strained composites; or stretchable but inelastic materials.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include loop fasteners and the second fastening components 84 include complementary hook fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side panels 134 overlapping the front side panels 34 upon connection thereto, which is convenient, the training pants 20 can also be configured so that the front side panels 34 overlap the back side panels 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side panels 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in FIG. 4, the absorbent article 20 is shown in an unfolded state illustrating the interior surface of the article, which faces the wearer during use. In FIG. 4, the absorbent article 20 further includes a surge management layer 60 which may be optionally located adjacent the liner 42 and/or the absorbent structure 44 and attached to various components in the article 20 such as the absorbent structure 44 or the bodyside liner 42 by methods known in the art, such as by using an adhesive. A surge management layer 60 helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As described above, the present invention is particularly directed to absorbent articles having controlled stretch properties. In particular, absorbent articles of the present invention demonstrate biaxial stretch characteristics in both the lateral direction and the longitudinal direction. Specifically, the absorbent articles have a biaxial stretch ratio of from about 1.0 to about 2.5. The biaxial stretch ratio is the ratio of percent stretch along the hip circumference of the article divided by the percent stretch of the article in the longitudinal direction.

Referring to FIG. 1, opposing arrows 92 are intended to illustrate stretch of the absorbent article 20 along the hip circumference. The hip circumference is located below the waist opening and is defined as the circumferential area that is generally parallel to the waist opening and comprises the lower two-thirds of the side panels. In other words, the hip circumference is a circumferential band that extends 66% of the distance from the top of the leg openings on the chassis to the waist opening (assuming the chassis does not include leg extensions that cover a portion of the wearer's legs).

For most applications, the percent stretch along the hip circumference can range from about 5% to about 150%, such as from about 20% to about 120%. In one embodiment, for instance, the percent stretch along the hip circumference as defined herein may be from about 30% to about 100%.

Referring to FIGS. 2 and 3, arrows 90 are intended to illustrate stretch of the article in the longitudinal direction 48. In general, the percent stretch in the longitudinal direction is generally the same or less than the percent stretch along the hip circumference. In some embodiments, for instance, the percent stretch in the longitudinal direction may be from about 5% to about 30%, such as from about 10% to about 25%. For example, in one particular embodiment, the percent stretch in the longitudinal direction may be from about 15% to about 20%.

As stated above, the overall biaxial stretch ratio can vary from about 1.0 to about 2.5. Of particular advantage, absorbent articles may be made in accordance with the present invention having tailored biaxial stretch ratios for particular products and end use applications. For example, for absorbent articles designed to absorb heavy liquid loadings, a lesser amount of longitudinal stretch may be desired in order to minimize and prevent sagging or drooping of the crotch region of the article when wet. In this embodiment, for instance, the biaxial stretch ratio may be less than about 1.3, such as from about 1.0 to about 1.3, and particularly from about 1.1 to about 1.3.

In an alternative embodiment, however, instead of designing the absorbent article with a lower biaxial stretch ratio, the longitudinal stretch may be concentrated in the waist zones of the product to prevent sagging and drooping when wet. In this embodiment, for instance, the biaxial stretch ratio may be greater than 1.3. The absorbent article, however, may include a front waist zone and a back waist zone that each comprise from about 15% to about 20% of the total length of the article. At least about 80%, such as at least about 90%, of the total amount of stretch contained in the absorbent article along the longitudinal direction may reside in the front and back waist zones. In this manner, not only does the absorbent article resist drooping and sagging when wet, but also remains capable of accommodating a relatively large range of sizes.

For absorbent articles designed to absorb lesser amounts of fluids, a greater amount of stretch may reside in the longitudinal direction. In these articles, for instance, the biaxial stretch ratio may be greater than about 1.3, such as from about 1.3 to about 2.5. In particular, in these applications, the biaxial stretch ratio may be from about 1.3 to about 2.0, such as from about 1.3 to about 1.4.

Various techniques may be used in order to produce the absorbent article 20 with the above stretch properties. In constructing absorbent articles in accordance with the present invention, for instance, the outer cover 40 may be elastic, while the bodyside liner 42 is stretchable or vice versa. In other embodiments, both the outer cover and the bodyside liner may be elastic. Depending upon the construction of the article, the absorbent structure 44 may also be stretchable and/or elastic.

In one particular embodiment, the outer cover 40 and/or the bodyside liner 42 are made from biaxially stretchable and/or elastic materials. These materials are incorporated into the absorbent article 20 in a manner that provides the article with the desired stretch characteristics in the longitudinal direction and the lateral direction.

The outer cover 40, the inner liner 42 and the absorbent structure 44 may be made from many different materials. All three layers, for instance, may be stretchable and/or elastic. Further, the stretch properties of each layer may vary in order to control the overall stretch properties of the product.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

In most embodiments, the outer cover 40 is biaxially stretchable and optionally biaxially elastic. Elastic non-woven laminate webs that can be used as the outer cover 40 include a non-woven material joined to one or more gatherable non-woven webs, films, or foams. Stretch Bonded Laminates (SBL) and Neck Bonded Laminates (NBL) are examples of elastomeric composites. Non-woven fabrics are any web of material which has been formed without the use of textile weaving processes which produce a structure of individual fibers that are interconnected in an integrating manner.

Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films, foams, meltblown fabrics or spunbond fabrics composed of polyethylene, polypropylene, or polyolefin elastomers, as well as combinations thereof. The elastomeric materials may include PEBAX elastomer (available from AtoChem located in Philadelphia, Pa.), HYTREL elastomeric polyester (available from Invista of Wilmington, Del.), KRATON elastomer (available from Kraton Polymers of Houston, Tex.), or strands of LYCRA elastomer (available from Invista of Wilmington, Del.), or the like, as well as combinations thereof. The outer cover 40 may include materials that have elastomeric properties through a mechanical process, printing process, heating process, or chemical treatment. For examples such materials may be apertured, creped, neck-stretched, heat activated, embossed, and microstrained; and may be in the form of films, webs, and laminates.

In particular aspects of the invention, the outer cover 40 may include a 0.4 ounces per square yard (osy) (13.6 grams per square meter (gsm)) basis weight layer of G2760 KRATON elastomer strands adhesively laminated with a 0.3 gsm layer of adhesive between two facings. Each facing can be composed of a thermal point bonded bicomponent spunbond non-woven fibrous web having a 0.7 osy (23.7 gsm) basis weight. The adhesive is similar to an adhesive which is supplied by Bostik Findley Adhesive and designated as H2525 A, and the elastomer strands are placed and distributed to provide approximately 12 strands of KRATON elastomer per inch (2.54 cm) of lateral width of the outer cover 40.

Alternatively, the outer cover 40 may include a woven or non-woven fibrous web layer which has been totally or partially constructed or treated to impart the desired levels of liquid impermeability to selected regions that are adjacent or proximate the absorbent structure. For example, the outer cover 40 may include a gas-permeable, non-woven fabric layer laminated to a polymer film layer which may or may not be gas-permeable. Other examples of fibrous, cloth-like outer cover 40 materials can include a stretch thinned or stretch thermal laminate material composed of a 0.6 mil (0.015 mm) thick polypropylene blown film and a 0.7 osy (23.8 gsm) polypropylene spunbond material (2 denier fibers).

Suitable materials for a biaxially stretchable outer cover 40 include biaxially stretchable material and biaxially elastic stretchable material. One example of a suitable outer cover material can include a 0.3 osy (10.2 gsm) polypropylene spunbond that is necked 60% in the lateral direction 49 and creped 60% in the longitudinal direction 48, laminated with 3 grams per square meter (gsm) Findley 2525A styrene-isoprene-styrene based adhesive to 8 gsm PEBAX 2533 film with 20% TiO$_2$ concentrate. The outer cover 40 can suitably be stretched, laterally and/or longitudinally, by at least 30% (to at least 130% of an initial (unstretched) width and/or length of the outer cover 40). More suitably, the outer cover 40 can be stretched laterally and/or longitudinally, by at least 50% (to at least 150% of the unstretched width or length of the outer cover 40). Even more suitably, the outer cover 40 can be stretched, laterally and/or longitudinally, by at least 100% (to at least 200% of the unstretched width or length of the outer cover 40). Tension force in the outer cover 40 at 50% extension is suitably between 50 and 1000 grams, more suitably between 100 and 600 grams, as measured on a 3 inch (7.62 cm) wide piece of the outer cover material.

Another example of a suitable material for a biaxially stretchable outer cover 40 is a breathable elastic film/nonwoven laminate, described in U.S. Pat. No. 5,883,028, issued to Morman et al., incorporated herein by reference to the extent that it is consistent (i.e. not in conflict) herewith. Examples of materials having two-way stretchability and retractability are disclosed in U.S. Pat. No. 5,116,662 issued to Morman and U.S. Pat. No. 5,114,781 issued to Morman, both of which are hereby incorporated herein by reference to the extent that it is consistent (i.e., not in conflict) herewith. These two patents describe composite elastic materials capable of stretching in at least two directions. The materials have at least one elastic sheet and at least one necked material, or reversibly necked material, joined to the elastic sheet at least at three locations arranged in a nonlinear configuration, so that the necked, or reversibly necked, web is gathered between at least two of those locations.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The bodyside liner 42 may also be stretchable, and more suitably it may be elastomeric. Suitable elastomeric materials for construction of the bodyside liner 42 can include elastic strands, LYCRA elastics, cast or blown elastic films, non-woven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers.

As an additional example, in one aspect the bodyside liner 42 suitably includes a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) are adhered to the necked spunbond material. The fabric is surface treated with an operative amount of surfactant, such as about 0.6 percent AHCOVEL Base N62 surfactant, available from ICI Americas, a business having offices in Wilmington, Del., U.S.A. The surfactant can be applied by any conventional means, such as spraying, printing, brush coating or the like. Other suitable materials may be extensible biaxially stretchable materials, such as a neck stretched/creped spunbond. The bodyside liner 42 can also be made from extensible materials as are described in U.S. Pat. No. 6,552,245 filed on May 3, 2000 by Roessler et al which is incorporated herein by reference. The bodyside liner 42 can also be made from biaxially stretchable materials as are described in U.S. Pat. No. 6,641,134 filed on Oct. 27, 2000 by Vukos et al which is incorporated herein by reference.

The liner 42 can suitably be stretched, laterally and/or longitudinally, by at least 30% (to at least 130% of an initial (unstretched) width and/or length of the liner 42). More suitably, the liner 42 can be stretched laterally and/or longitudinally, by at least 50% (to at least 150% of the unstretched width or length of the liner 42). Even more suitably, the liner 42 can be stretched, laterally and/or longitudinally, by at least 100% (to at least 200% of the unstretched width or length of the liner 42). Tension force in the liner 42 at 50% extension is suitably between 50 and 1000 grams, more suitably between 100 and 600 grams, as measured on a 3 inch (7.62 cm) wide piece of the liner material.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference to the extent they are consistent (i.e., not in conflict) herewith.

In a particular aspect of the absorbent article of the present invention, the absorbent structure 44 may also be elastic. For this purpose, the absorbent web material can include elastomeric fibers in an amount which is at least a minimum of about 2 wt %. The amount of elastomeric fibers can alternatively be at least about 3 wt %, and can optionally be at least about 5 wt % to provide improved performance. In addition, the amount of elastomeric fibers can be not more than about 60 wt %. Alternatively, the amount of elastomeric fibers can be not more than about 45 wt %, and optionally, can be not more than about 30 wt % to provide improved benefits. These values may impact the absorbent structure 44 by affecting the desired levels of stretchability and structural stability without excessively degrading the physical properties or the liquid-management properties of the absorbent structure. An absorbent web material with an excessively low proportion of elastomeric fibers may be insufficiently stretchable, and a web material with an excessively high proportion of elastomeric fibers may exhibit an excessive degradation of its absorbency functionalities, such as poor intake, poor distribution, poor retention of liquid.

The absorbent structure 44 may include an elastomeric coform absorbent web material. Such materials are described for instance in U.S. Pat. Nos. 6,231,557 B1 and 6,362,389 B1, which are each incorporated by reference herein to the extent they are consistent (i.e., not in conflict) herewith. In particular aspects, the elastomeric coform material can have an overall coform basis weight of at least about 50 gsm, such as up to about 1200 gsm. The coform basis weight, for example, may be at least about 100 gsm, such as at least about 200 gsm. These values can provide the absorbent structure with the desired stretchability and structural stability without excessively degrading the physical properties or the liquid-management functionalities of the absorbent structure. For example, retention portions having excessively low proportions of elastomeric coform material may not be sufficiently stretchable. Conversely, an absorbent web material having excessively large amounts of elastomeric coform materials can exhibit an excessive degradation of their absorbency functionalities, such as an excessive degradation of intake, distribution and/or retention properties.

Other examples of usable elastomeric absorbent bodies are described in international patent application WO 03/051254 and U.S. Pat. Nos. 5,964,743, 5,645,542, 6,231,557, and 6,362,389 B1, each of which are incorporated by reference herein to the extent they are consistent (i.e., not in conflict) herewith.

Test Procedures

As described above, absorbent articles made in accordance with the present invention have a biaxial stretch ratio within a particular range. The biaxial stretch ratio is determined by measuring the percent stretch along the hip circumference and the percent stretch in the longitudinal direction of the product. The following test procedures are provided for calculating biaxial stretch ratios in accordance with the present invention.

Percent Stretch Along the Hip Circumference

This procedure is a single-cycle tension bench test to measure hip circumference and length of a test pant. The pant is tested in the state in which it is provided to the consumer, intended for immediate donning. A test pant is cycled to a specific loading rather than to a fixed elongation/extension.

Data generated by this test method includes:
Hip circumference (mm) at an initial load of 70 g.
Hip circumference (mm) at a load of 2000 g.

To measure product hip circumference, in one embodiment, a pair of u-shaped bars are threaded on each side of the product. In particular, one leg of each u-shaped bar is inserted in the waist opening and through a leg opening. The opposite leg of each u-shaped bar includes an attachment device for attaching the bar to a testing machine. For instance, one bar may be attached to a top jaw while the other bar may be attached to a bottom jaw on the testing device. When the bars are moved in opposite directions, a load is placed on the hip circumference. In one embodiment, the product may be trimmed so that only the hip circumference is placed between the bars.

The gage length is selected for the pant being tested, so as to provide a tension of between 0 and 65 grams (g) when the pant is positioned for the test, prior to the start of the test. The term tension refers to the gram value measured by the load cells in the tensile tester.

The jaws are separated until a load of 70 (TBD) grams of tension is attained, at which tension the gage length is recorded. Then the jaws continue to move apart until 2,000 (TBD) grams of tension is reached, at which tension the gage length is again recorded. The standard test is one cycle per pant. The circumference at a given tension may be calculated using the gage length and the circumference value(s) for the upper and lower bars. Desirably at least five specimens are tested. The hip circumference values at 2000 (TBD) grams tension from each specimen tested are averaged to obtain an average hip circumference for a given sample.

Apparatus and Materials

1. Constant Rate of Extension (CRE) tensile tester: MTS tensile tester Systems Corporation, 7 model Synergie 200 Test Bed; available from MTS Research Triangle Park, N.C. USA.

2. Load cells: A suitable cell selected so the majority of the peak load values fall between the manufacturer's recommended ranges of load cell's full Systems Corporation, 7 scale value; Model 100N available from MTS Research Triangle Park, N.C. USA.

3. Operating software and data acquisition system: MTS TestWorks® for Systems 7 Windows software version 4.06A, build 617; available from MTS Corporation, Research Triangle Park, N.C. USA.

4. Grips: pneumatic-action grips, top and bottom, identified as part number 2712-003 available from Instron Corporation, Canton, Mass. USA.

5. Grip faces: 25 by 75-mm (1 by 3-inch), suitable for holding pins.

6. Pins: rigid pins having a length of 6.3 centimeters (2.5 inch) and a knurled portion at one end for holding specimens, the knurled portion having an outside diameter of 6.4 millimeters (0.25 inch) and a length of 3.2 centimeters (1.25 inch).≅wide by ⅜≅2.7 Clips (optional): 1.9 cm. wide by 0.95 cm. capacity (¾ capacity) binder clips; part no. BTM00251 available from BT Office Products, Milwaukee, Wis., USA.

Conditioning

Conduct test in standard ASTM laboratory conditions: atmosphere of 23±2° C. (73.4±3.6° F.) and 50±5% relative humidity. The products should be measured after they equilibrate to laboratory conditions.

Test Specimen

No preparation needed. The whole article is tested.

Procedure

Tensile Tester test conditions:

Data acquisition rate . . . 100.0 Hz
Perform PreLoad (PreCond)? . . . No
Perform PreConditioning? . . . No
Perform PreLoad?: . . . No
Cross head speed: . . . 500 mm/min
Gage length: Appropriate starting gage length settings for both hip and waistband are those that will generate initial loads of between 0 and 65 g in a previously untested product
Go to load (cycle trigger): . . . 2000 g (or a maximum load value that can be experienced by the sample without causing the sample to tear or otherwise come apart)
Break sensitivity: . . . 90%

A. Install pin assemblies as described above

B. Using the tensile frame pushbutton controls for crosshead position, move pins so that the pant can be mounted on the pins without stretching the pant. Determine the gage length by measuring from the centerline of the first pin to the centerline of the second pin. Calibrate the software to this initial gage length.

C. Place the waistband onto the knurled section of the top pin. Center one side of the pant on top of the pin. Use a single binder clip to hold the pant at the waist opening in place on the pin; do not stretch the pant during application of the clip.

D. Click on ZERO to tare the load of the pant. Only tare the weight of the first pant for each sample population, not for each specimen.

E. Place the waistband on the opposite side of the pant on the bottom pin and clip in place as for the first pin. Adjust pant so both top and bottom pins are inserted 2.5 centimeters (1 inch) into the pant.

F. Using the tensile frame pushbutton controls for crosshead position, move pins apart until the load applied to the waistband is between 0 and 65 g.

G. Click on RUN button. The test will start automatically.

H. When the test is done, click on either FILE to save the data and graphs or NEXT to save only the data.

I. Remove the sample from the pins.

J. Repeat steps B, C and E through I for each specimen until the testing is complete.

The circumference of a measured waistband at any tension may be calculated by multiplying the gage length at that tension by 2, and adding one half the circumference of the upper pin and one half the circumference of the lower pin;

The percent hip stretch of the product is determined by:

$$\{[Hip\ circumference\ at\ 2000\ g-Hip\ circumference\ at\ 70\ g]/Hip\ circumference\ at\ 70\ g \times 100$$

Percent Stretch in the Longitudinal Direction

Data generated by this test method includes:
Product length (mm) an initial load of 70 g.
Product length (mm) at a load of 500 g.

The product has a length dimension measured between the front and back end edges along the longitudinal axis. This corresponds to the rise dimension of a garment.

A suitable method for determining the longitudinal length of the product is to hang the product vertically adjacent a flat, vertical surface. Prior to hanging, the product is opened by cutting or opening any side seams. The product is hung with the back region above the front region and with the surface intended to face the wearer's outer garments during use positioned toward the flat, vertical surface. The top end margin of the product is held horizontal with two clamps, the inner edges of which are spaced 3.5 inches (8.9 cm) apart. The clamps are positioned if possible to avoid any absorbent within the product, and are symmetrically disposed with respect to the longitudinal centerline/axis of the product. Any waist elastic present in the product is stretched to the point that it stops elastically stretching prior to securing the clamps.

The lower end of the hanging product (front waistband region) is clamped with a jig weighing 70 g. The jig possesses two clamp units (medium 20×12 inches, B-inch 3 size, Bulldog clips, 2⅛ inch) attached to a tie rod (coarse thread, zinc plated), the clamps symmetrically placed with respect to the longitudinal centerline of the product, with a spacing between internal edges of –inch nut placed at the inner and 3 the clamps of 3.5 inches (8.9 cm), with outer edges of each clamp to hold the clamps in place. One (capped) bottle (1-ounce plastic screw cap bottle, such as NALGENE brand) is attached to each clamp with a piece of string. The assembly is placed on a laboratory balance and lead shot (No. 5 chilled lead shot, such as LAWRENCE brand) is added to each bottle (in equal amounts) until the total weight of the jig is as close to 70 grams as possible. The jig is attached to the lower end of the hanging product, stretching any waist band as mentioned above.

The product length (mm) at an initial load is then determined by measuring the distance between the front and back end edges along the longitudinal centerline/axis, between the clamps. All measurements are taken within 30 seconds of hanging the jig. Five specimens of each code are analyzed, and the results for each code are averaged to obtain the average product length (mm) an initial load of 70 g.

The 70 gram jig is then removed and a 500 g jig of the same construction is then hung on the bottom of the product in the same manner described for the 70 g jig. The product length (mm) at the 500 g load is then determined by measuring the distance between the front and back end edges along the longitudinal centerline/axis, between the clamps. All measurements are taken within 30 seconds of hanging the jig. Five specimens of each code are analyzed, and the results for each code are averaged to obtain the average product length (mm) at a 500 g load.

The percent longitudinal stretch of the product is determined by:

{[length at 500 g load−length at 70 g load]/length at 70 g load}×100

Biaxial Stretch Ratio

From the above measurements, the biaxial stretch ratio can be determined as follows:

$$\text{Biaxial Stretch Ratio} = \frac{\% \text{ Stretch Along the Hip Circumference}}{\% \text{ Stretch in the Longitudinal Direction}}$$

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A biaxially stretchable absorbent article comprising:
an outer cover;
a bodyside liner joined to the outer cover in a superimposed relation;
an absorbent structure positioned in between the outer cover and the liner; and
wherein the absorbent article includes a front region, a back region and a crotch region, the front region and back region defining a waist opening when worn about a wearer, the crotch region being positioned in between two leg openings that are located opposite the waist opening, the absorbent article including a longitudinal direction extending from the front region, through the crotch region and to the back region, and a lateral direction generally parallel to the circumference of the waist opening and perpendicular to the longitudinal direction, the absorbent article including a hip circumference in the lateral direction that is located so as to circumscribe the hips of a wearer and wherein the absorbent article is stretchable so as to have a biaxial stretch ratio of from about 1.0 to about 2.5, the biaxial stretch ratio being defined by the formula:

$$\text{Biaxial Stretch Ratio} = \frac{\% \text{ Stretch Along the Hip Circumference}}{\% \text{ Stretch in the Longitudinal Direction}}$$

wherein:

$$\begin{array}{l}\% \text{ Stretch Along} \\ \text{the Hip Circumference}\end{array} = \frac{\left(\begin{array}{l}\text{Hip Circumference at 2000 g} - \\ \text{Hip Circumference at 70 g}\end{array}\right)}{\text{Hip Circumference at 70 g}} \times 100$$

$$\begin{array}{l}\% \text{ Stretch in the} \\ \text{Longitudinal Direction}\end{array} = \frac{\left(\begin{array}{l}\text{Length of Article at 500 g} - \\ \text{Length of Article at 70 g}\end{array}\right)}{\text{Length of Article at 70 g}} \times 100.$$

2. A biaxially stretchable absorbent article as defined in claim 1, wherein the article has a biaxial stretch ratio of from about 1.0 to about 1.3.

3. A biaxially stretchable absorbent article as defined in claim 1, wherein the article has a biaxial stretch ratio of from about 1.3 to about 2.0.

4. A biaxially stretchable absorbent article as defined in claim 1, wherein the article has a biaxial stretch ratio of from about 1.1 to about 1.5.

5. A biaxially stretchable absorbent article as defined in claim 1, wherein the article has a biaxial stretch ratio of from about 1.1 to about 1.3.

6. A biaxially stretchable absorbent article as defined in claim 1, wherein the article has a biaxial stretch ratio of from about 1.3 to about 1.4.

7. A biaxially stretchable absorbent article as defined in claim 1, wherein the outer cover is biaxially stretchable.

8. A biaxially stretchable absorbent article as defined in claim 1, wherein the outer cover is biaxially elastic.

9. A biaxially stretchable absorbent article as defined in claim 1, wherein the outer cover, bodyside liner and absorbent structure form a chassis and wherein the absorbent article further comprises opposing pairs of front and back side panels attached to the chassis, the front and back side panels for attaching the chassis around the torso of a wearer.

10. A biaxially stretchable absorbent article as defined in claim 8, wherein the liner is biaxially stretchable.

11. A biaxially stretchable absorbent article as defined in claim 1, wherein the percent stretch in the longitudinal direction of the article is from about 5% to about 30%.

12. A biaxially stretchable absorbent article as defined in claim 1, wherein the percent stretch in the longitudinal direction of the article is from about 10% to about 25%.

13. A biaxially stretchable absorbent article as defined in claim 11, wherein the article includes a front waist zone and a back waist zone, each waist zone comprising from about 15% to about 20% of the total length of the absorbent article, and wherein at least 80% of the percent stretch in the longitudinal direction of the article resides in the waist zones.

14. A biaxially stretchable absorbent article as defined in claim 11, wherein the article includes a front waist zone and a back waist zone, each waist zone comprising from about 15% to about 20% of the total length of the absorbent article, and wherein at least 90% of the percent stretch in the longitudinal direction of the article resides in the waist zones.

15. A biaxially stretchable absorbent article as defined in claim 9, wherein each pair of side panels includes an attachment device for releasably attaching the corresponding side panels together.

16. An absorbent article comprising:
a biaxially stretchable outer cover, the outer cover comprising a film or a laminate containing a nonwoven material;
a biaxially stretchable bodyside liner joined to the outer cover in a superimposed relation;
an absorbent structure positioned in between the outer cover and the liner;
and wherein the absorbent article includes a front region, a back region and a crotch region, the front region and back region defining a waist opening when worn about a wearer, the crotch region being positioned in between two leg openings that are located opposite the waist opening, the absorbent article including a longitudinal direction extending from the front region, through the crotch region and to the back region, and a lateral direction generally parallel to the circumference of the waist opening and perpendicular to the longitudinal direction, the absorbent article including a hip circumference in the lateral direction that is located so as to circumscribe the hips of a wearer and wherein the absorbent article is stretchable so as to have a biaxial stretch ratio of from about 1.1 to about 1.5, the biaxial stretch ratio being defined by the formula:

$$\text{Biaxial Stretch Ratio} = \frac{\text{\% Stretch Along the Hip Circumference}}{\text{\% Stretch in the Longitudinal Direction}}$$

wherein:

$$\text{\% Stretch Along the Hip Circumference} = \frac{\left(\text{Hip Circumference at 2000 g} - \text{Hip Circumference at 70 g}\right)}{\text{Hip Circumference at 70 g}} \times 100$$

$$\text{\% Stretch in the Longitudinal Direction} = \frac{\left(\text{Length of Article at 500 g} - \text{Length of Article at 70 g}\right)}{\text{Length of Article at 70 g}} \times 100.$$

17. An absorbent article as defined in claim 16, wherein the outer cover is elastic.

18. An absorbent article as defined in claim 16, wherein the liner is elastic.

19. An absorbent article as defined in claim 16, wherein the article has a biaxial stretch ratio of from about 1.1 to about 1.3.

20. An absorbent article as defined in claim 16, wherein the article has a biaxial stretch ratio of from about 1.3 to about 1.4.

21. An absorbent article as defined in claim 16, wherein the outer cover, bodyside liner and absorbent structure form a chassis and wherein the chassis is responsible for all stretch in the longitudinal direction.

22. An absorbent article as defined in claim 16, wherein the percent stretch in the longitudinal direction of the article is from about 5% to about 30%.

23. An absorbent article as defined in claim 16, wherein the percent stretch in the longitudinal direction of the article is from about 10% to about 25%.

24. An absorbent article as defined in claim 22, wherein the article includes a front waist zone and a back waist zone, each waist zone comprising from about 15% to about 20% of the total length of the absorbent article, and wherein at least 80% of the percent stretch in the longitudinal direction of the article resides in the waist zones.

25. An absorbent article as defined in claim 22, wherein the article includes a front waist zone and a back waist zone, each waist zone comprising from about 15% to about 20% of the total length of the absorbent article, and wherein at least 90% of the percent stretch in the longitudinal direction of the article resides in the waist zones.

26. A biaxially stretchable absorbent article comprising:
a chassis comprising a biaxially elastic outer cover, a biaxially stretchable bodyside liner and an absorbent structure positioned in between the outer cover and the liner, the outer cover comprising a film or a laminate containing a nonwoven material, the absorbent structure containing superabsorbent particles;
opposing pairs of front and back side panels attached to the chassis, the side panels for securing the article around the torso of a wearer;
the absorbent article including a front region, a back region, and a crotch region, the front region and the back region defining a waist opening when worn about a wearer, the crotch region being positioned between two leg openings that are located opposite the waist opening, the absorbent article including a longitudinal direction extending from the front region through the crotch region to the back region and a lateral direction generally parallel to the circumference of the waist opening and perpendicular to the longitudinal direction, the absorbent article including a hip circumference in the lateral direction that is located so as to circumscribe the hips of a wearer;
a pair of elastic containment flaps connected to the chassis that extend generally in the longitudinal direction in at least the crotch region;
a pair of leg elastic members that at least partially surround each of the leg openings;
and wherein the absorbent article is stretchable so as to have a biaxial stretch ratio of from about 1.0 to about 2.5, the biaxial stretch ratio being defined by the formula:

$$\text{Biaxial Stretch Ratio} = \frac{\text{\% Stretch Along the Hip Circumference}}{\text{\% Stretch in the Longitudinal Direction}}$$

wherein:

% Stretch Along the Hip Circumference =

$$\frac{(\text{Hip Circumference at 2000 g} - \text{Hip Circumference at 70 g})}{\text{Hip Circumference at 70 g}} \times 100$$

% Stretch in the Longitudinal Direction =

$$\frac{(\text{Length of Article at 500 g} - \text{Length of Article at 70 g})}{\text{Length of Article at 70 g}} \times 100.$$

27. A biaxially stretchable absorbent article as defined in claim 26, wherein the article has a biaxial stretch ratio of from about 1.1 to about 1.5.

28. A biaxially stretchable absorbent article as defined in claim 26, wherein the percent stretch in the longitudinal direction of the article is from about 5% to about 30%.

29. A biaxially stretchable absorbent article as defined in claim 28, wherein the article includes a front waist zone and a back waist zone, each waist zone comprising from about 15% to about 20% of the total length of the absorbent article, and wherein at least 80% of the percent stretch in the longitudinal direction of the article resides in the waist zones.

30. A biaxially stretchable absorbent article as defined in claim 28, wherein the article includes a front waist zone and a back waist zone, each waist zone comprising from about 15% to about 20% of the total length of the absorbent article, and wherein at least 90% of the percent stretch in the longitudinal direction of the article resides in the waist zones.

* * * * *